(12) United States Patent
Gupta et al.

(10) Patent No.: US 7,625,754 B2
(45) Date of Patent: Dec. 1, 2009

(54) CONTINUOUS CULTURE OF CONIFER EMBRYOGENIC TISSUE

(75) Inventors: Pramod K. Gupta, Federal Way, WA (US); Diane G. Holmstrom, Sumner, WA (US); Bonnie Larson, Granite Falls, WA (US)

(73) Assignee: Weyerhaeuser NR Company, Federal Way, WA (US)

( * ) Notice: Subject to any disclaimer, the term of this patent is extended or adjusted under 35 U.S.C. 154(b) by 385 days.

(21) Appl. No.: 11/063,416

(22) Filed: Feb. 22, 2005

(65) Prior Publication Data

US 2005/0188436 A1 Aug. 25, 2005

Related U.S. Application Data

(60) Provisional application No. 60/547,475, filed on Feb. 25, 2004.

(51) Int. Cl.
*C12N 5/02* (2006.01)
(52) U.S. Cl. ........................................ 435/422; 435/410
(58) Field of Classification Search ................. 435/422, 435/410
See application file for complete search history.

(56) References Cited

U.S. PATENT DOCUMENTS

| | | | |
|---|---|---|---|
| 4,217,730 A | 8/1980 | Abo El-Nil |
| 4,801,545 A | 1/1989 | Stuart et al. |
| 4,957,866 A | 9/1990 | Gupta et al. |
| 5,034,326 A | 7/1991 | Pullman et al. |
| 5,036,007 A | 7/1991 | Gupta et al. |
| 5,041,382 A | 8/1991 | Gupta et al. |
| 5,183,757 A | 2/1993 | Roberts |
| 5,187,092 A | 2/1993 | Uddin |
| 5,236,841 A | 8/1993 | Gupta et al. |
| 5,238,835 A | 8/1993 | McKersie et al. |
| 5,294,549 A | 3/1994 | Pullman et al. |
| 5,413,930 A | 5/1995 | Becwar et al. |
| 5,464,769 A | 11/1995 | Attree et al. |
| 5,482,857 A | 1/1996 | Gupta et al. |
| 5,491,090 A | 2/1996 | Handley, III et al. |
| 5,501,972 A | 3/1996 | Westcott |
| 5,506,136 A | 4/1996 | Becwar et al. |
| 5,523,230 A | 6/1996 | Smith |
| 5,534,433 A | 7/1996 | Coke |
| 5,534,434 A | 7/1996 | Coke |
| 5,563,061 A | 10/1996 | Gupta |
| 5,564,224 A | 10/1996 | Carlson et al. |
| 5,565,355 A | 10/1996 | Smith |
| 5,587,312 A | 12/1996 | van Holst et al. |
| 5,610,051 A | 3/1997 | Becwar et al. |
| 5,677,185 A | 10/1997 | Handley, III |
| 5,731,191 A | 3/1998 | Rutter et al. |
| 5,731,203 A | 3/1998 | Handley, III |
| 5,731,204 A | 3/1998 | Rutter et al. |
| 5,821,126 A | 10/1998 | Durzan et al. |
| 5,840,581 A | 11/1998 | Carraway et al. |
| 5,850,032 A | 12/1998 | Wann |
| 5,856,191 A | 1/1999 | Handley, III |
| 5,985,667 A | 11/1999 | Attree et al. |
| 6,022,744 A | 2/2000 | Tetteroo et al. |
| 6,117,678 A | 9/2000 | Carpenter et al. |
| 6,134,830 A | 10/2000 | Welty |
| 6,150,167 A | 11/2000 | Carpenter et al. |
| 6,180,405 B1 | 1/2001 | Aitken-Christie et al. |
| 6,200,809 B1 | 3/2001 | Klimaszewska et al. |
| 6,340,594 B1 | 1/2002 | Attree et al. |
| 6,372,496 B1 | 4/2002 | Attree et al. |
| 6,417,001 B2 | 7/2002 | Aitken-Christie et al. |
| 6,444,467 B1 | 9/2002 | Fan et al. |
| 6,492,174 B1 | 12/2002 | Pullman et al. |
| 6,893,873 B2 * | 5/2005 | Pullman ..................... 435/422 |
| 7,235,402 B2 | 6/2007 | Aubry et al. |
| 2002/0012994 A1 | 1/2002 | Aitken-Christie et al. |
| 2002/0092037 A1 | 7/2002 | Connett-Porceddu et al. |
| 2002/0100083 A1 | 7/2002 | Connett-Porceddu et al. |
| 2003/0153080 A1 | 8/2003 | Pullman |

FOREIGN PATENT DOCUMENTS

| | | |
|---|---|---|
| CA | 2293945 | 8/2003 |
| EP | 0 300 730 B1 | 1/1989 |
| EP | 0 618 766 B1 | 10/1994 |
| EP | 0 934 691 A2 | 8/1999 |
| WO | WO 95/33822 A1 | 12/1995 |
| WO | WO 98/48279 A1 | 10/1998 |
| WO | WO 99/46977 | 9/1999 |
| WO | WO 01/20972 A1 | 9/2000 |

OTHER PUBLICATIONS

Hale et al.; "Bioreactor Development for Continual-flow, Liquid Plant Tissue," Acta Horticulturae, 319, International Symposium Transplant Production Systems; 1992, pp. 107-112 (6 pages total).*
van Gulik et al.; "The application of continuous culture for plant cell suspensions." Enzyme and Microbial Technology, 28, (2001) pp. 796-805 (10 pages total).*
Bozhkov Pv et al., "A pronounced synergistic effect of abscisic acid and 6-benzyladenine on Norway spruce (*Picea abies* L. Karst) somatic embryo maturation," *Plant Cell Rep* (1992) pp. 386-389.
Attree, S.M. et al., "Somatic Embryo Maturation, Germination, and Soil Establishment of Plants of Black and White Spruce (*Picea mariana* and *Picea glauca*)," *Can. J. Bot.* 68:2583-2589, 1990.
Attree, S.M., et al., "Initiation of Embryogenic Callus and Suspension Cultures, and Improved Embryo Regeneration of Protoplasts, of White Spruce (*Picea glauca*)," *Can. J. Bot.* 67:1790-1795, 1989,.

(Continued)

*Primary Examiner*—Susan B McCormick Ewoldt
(74) *Attorney, Agent, or Firm*—Christensen O'Connor Johnson Kindness PLLC

(57) ABSTRACT

The present invention provides methods for multiplying conifer embryogenic tissue. The methods of the present invention each include the step of continuously culturing conifer embryogenic tissue in liquid multiplication medium for a period of time sufficient for the embryogenic tissue to multiply.

9 Claims, 1 Drawing Sheet

OTHER PUBLICATIONS

Attree, S.M., et al., "Plantlet Regeneration From Embryogenic Protoplasts of White Spruce (*Picea glauca*)," *Bio/Technology* 7:1060-1062, 1989.

Boulay, M.P., et al., "Development of Somatic Embryos From Cell Suspension Cultures of Norway Spruce (*Picea abies* Karst.)," *Plant Cell Reports* 7:134-137, 1988.

Cornu, D. and C. Geoffrion, "Aspects of Somatic Embryogenesis in Larch Trees," *Bull. Soc. Bot. Fr.*, 137 Actual. Bot. (3/4):25-34, 1990 [translation].

Garin E et al, "Effects of sugars, amino acids, and culture technique on maturation of somatic embryos of Pinus strobes on medium with two gellan gum concentrations," *Plant Cell Tiss & Org Cult* (62) 27-27, 2000.

Gupta, P.K., et al., "Scale-Up Somatic Embryogenesis of Conifers For Reforestation," Proceedings of the 3rd Canadian Workshop on Plant Tissue Culture and Genetic Engineering, University of Guelph, Symposium 1: Somatic Embryogenesis and Synthetic Seeds, Abstract, Jun. 1992.

Hakman, I. and L.C. Fowke, "An Embryogenic Cell Suspension Culture of *Picea glauca* (White Spruce)," *Plant Cell Reports* 6:20-22, 1987.

Jain, S.M., et al., Forestry Sciences: Somatic Embryogenesis in Woody Plants, vol. 3, Gymnosperms, Kluwer Academic Publishers, Netherlands, 1995.

Keinonen-Mettälä, K., et al., "Somatic Embryogenesis of *Pinus sylvestris*," Scand. J. For. Res. 11:242-250, 1996.

Klimaszewska K et al, "Maturation of somatic embryos of pinus strobes is promoted by a high concentration of gellan gum," *Physiologica Plantarum* (100) 949-957, 1997.

Krogstrup, P. "Somatic Embryogenesis in Sitka Spruce (*Picea sitchensis* (Bong.) Carr.)," *Plant Cell Reports* 7:594-597, 1988.

Lelu Ma et al, "Somatic embryogenesis and plantlet development in *Pinus sylvestris* and *Pinus pinaster* on median with and without growth regulators," *Phys Plantarum, Munksgaard Intl* (105) 719-718, 1999.

Lelu, M.A. et al., "Effect of Maturation Duration on Desiccation Tolerance on Hybrid Larch (*Larix X leptoeuropaea* dengler) Somatic Embryos," *In Vitro Cell. Dev. Biol.* 3115-20, 1995.

Lu, C.-Y. and T.A. Thorpe, "Somatic Embryogenesis and Plantlet Regeneration in Cultured Immature Embryos of *Picea glauca*," *J. Plant Physiol.* 128:297-302, 1987.

Mathur, G. et al., "Studies on Somatic Embryogenesis From Immature Zygotic Embryos of CHIR Pine (*Pinus roxburghii* Sarg)," *Current Science* 79(7):999-1004, 2000.

Norgaard, J.V., and P. Krogstrup, "Cytokinin Induced Somatic Embryogenesis From Immature Embryos of *Abies nordmanniana* Lk.," *Plant Cell Reports* 9:509-513, 1991.

Ramarosandtradana LH et al, "Effects of Carbohydrate Source, Polyethylene Glycol and Gellan Gum Concentration on Embryonal-Suspensor Mass (ESM) Proliferation and Maturation of Maritime Pine Somatic Embryos," *In vitro Cellular and Developmental Biology-Plant* 37:29-34.

Roberts, D.R., "Abscisic Acid and Mannitol Promote Early Development, Maturation and Storage Protein Accumulation in Somatic Embryos of Interior Spruce," *Physiologia Plantarum* 83:247-254, 1991.

Roberts, D.R et al., "Interaction Between Maturation and High Relative Humidity Treatments and Their Effects on Germination of Sitka Spruce Somatic Embryos," *J. Plant Physiol.* 138:1-6, 1991.

Roberts, D.R., et al., "Synchronous and High Frequency Germination of Interior Spruce Somatic Embryos Following Partial Drying at High Relative Humidity," *Can. J. Bot.* 68:1086-1090, 1989.

Taber RP et al., "Kinetics of Douglas-fir (*Pseudotsunga menziesii*) somatic embryo development," *Can J Bot* (76): 838-871, 1998.

Thompson, R.G. and P. von Aderkas, "Somatic Embryogenesis and Plant Regeneration From Mature Embryos of Western Larch," *Plant Cell Reports* 11:379-386, 1992.

Timmis, R., "Bioprocessing for Tree Production in the Forest Industry: Conifer Somatic Embryogenesis," Biotechnol. Prog. 14(1):156-166, 1998.

Von Aderkas, P., et al., "Charcoal Affects Early Development and Hormonal Concentrations of Somatic Embryos of Hybrid Larch," Tree Physiology 22:431-434, 2002.

Von Arnold, S. and I. Hakman, "Regulation of Somatic Embryo Development in *Picea abies* by Abscisic Acid (ABA)," *J. Plant Physiol.* 132:164-169, 1988.

Von Arnold, S. and T. Eriksson, "A Revised Medium for Growth of Pea Mesophyll Protoplasts," *Physiol. Plant* 39:257-260, 1977.

Webb, D.T., et al., "Factors Influencing the Induction of Embryogenic and Caulogenic Callus From Embros of *Picea glauca* and *P. engelmanii*," *Can. J. For. Res.* 19:1303-1308, 1989.

* cited by examiner

CONTINUOUS CULTURE OF CONIFER EMBRYOGENIC TISSUE

CROSS REFERENCE TO RELATED APPLICATION

The present application claims the benefit of U.S. Provisional Application No. 60/547,475, filed Feb. 25, 2004.

FIELD OF THE INVENTION

The present invention relates to methods for producing plant embryos in vitro, and optionally producing plants from the plant embryos.

BACKGROUND OF THE INVENTION

The demand for conifer trees (e.g., pines and firs) to make wood products continues to increase. One proposed solution to this problem is to identify individual trees that possess desirable characteristics, such as a rapid rate of growth, and produce numerous, genetically identical, clones of the superior trees by somatic cloning. Somatic cloning is the process of producing plant embryos, in vitro, from plant cells that are not zygotes. These clones can be cultivated to yield stands, or whole forests, of conifer trees that possess the desirable characteristic(s).

One method for somatically cloning conifer trees uses in vitro treatment of isolated, living, conifer tissue under conditions that promote formation of conifer somatic embryos, and then whole plants, from the treated tissue. The isolated conifer tissue may be cultured in the presence of one or more auxins, and/or cytokinins, to promote formation and multiplication of embryogenic tissue that is then cultured under conditions that promote formation of cotyledonary conifer embryos. The embryos may then be germinated to yield conifer trees. An example of conifer embryogenic tissue are embryonal suspensor masses (ESMs) that can be formed, by tissue culture in vitro, from conifer embryos dissected from conifer seeds. By way of example, FIG. 1 shows pine embryonal suspensor masses in liquid culture. FIG. 2 shows a cotyledonary, pine, somatic embryo formed from ESM (cotyledons are visible at the top of the embryo).

A continuing problem, however, is stimulating efficient formation of cotyledonary conifer somatic embryos that are capable of germinating with high frequency to yield conifer plants. Preferably, the cotyledonary conifer somatic embryos, formed in vitro, are morphologically, anatomically, and biochemically similar, or identical, to zygotic conifer embryos formed, in vivo, in conifer seeds of the same species. In particular, there is a need for methods for producing, in vitro, greater numbers of zygotic-like cotyledonary conifer somatic embryos than are produced by prior art methods. Preferably, the germination frequency and quality of the cotyledonary conifer somatic embryos produced by the novel methods should be higher than the germination frequency and quality of cotyledonary conifer somatic embryos produced by prior art methods.

SUMMARY OF THE INVENTION

In accordance with the foregoing, the present invention provides methods for multiplying conifer embryogenic tissue in vitro. The methods of the present invention each includes the step of continuously culturing conifer embryogenic tissue in liquid multiplication medium for a period of time sufficient for the embryogenic tissue to multiply.

The methods of the invention are useful, for example, for multiplying conifer embryogenic tissue in vitro. The multiplied embryogenic tissue may be further cultured to produce conifer cotyledonary somatic embryos that may be germinated and grown to produce conifer trees. Thus, the methods of the invention facilitate production of conifer trees having desired properties (e.g., increased growth rate), and thereby help to satisfy the demand for lumber and wood products.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Figure 1:
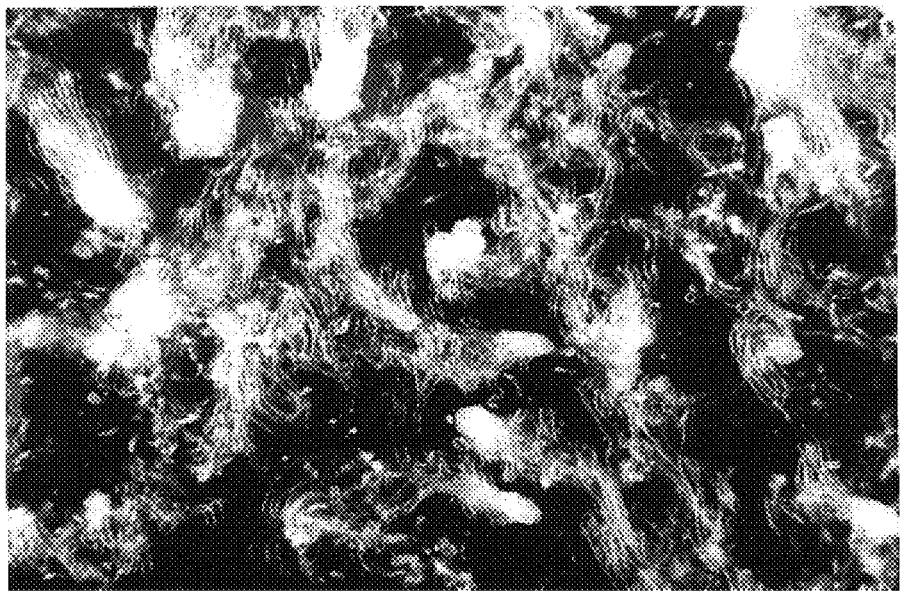
FIG. 1 shows pine embryonal suspensor masses in liquid culture.
Figure 2:
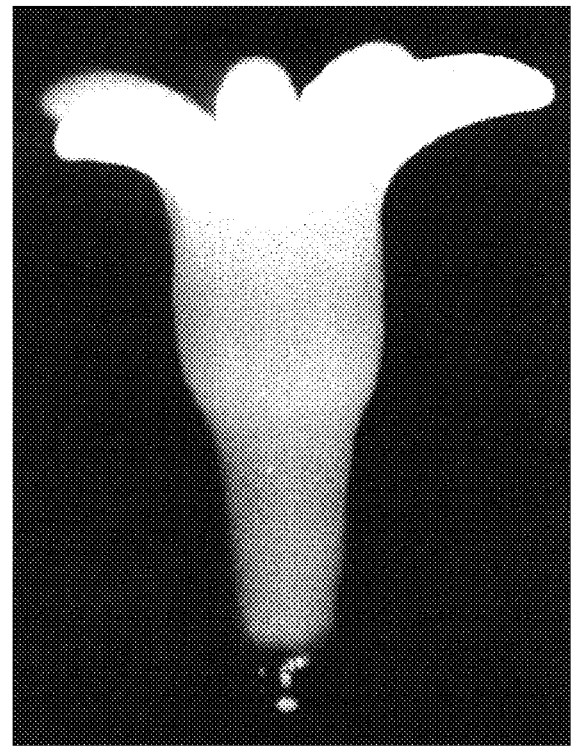
FIG. 2 shows a cotyledonary pine somatic embryo formed from ESM (cotyledons are visible at the top of the embryo).

As used herein, the term "cotyledonary embryo" means an embryo that possesses one or more cotyledons.

As used herein, the term "somatic embryo" refers to a plant embryo that developed in vitro from a plant cell that is not a zygote.

As used herein, the term "embryogenic tissue" refers to any tissue, derived from a conifer, which is capable of producing one or more cotyledonary conifer somatic embryos when treated in accordance with the methods of the invention. Thus, the term "embryogenic tissue" includes, for example, conifer embryonal suspensor masses.

As used herein, the term "multiplication medium" refers to a liquid medium that is formulated to promote the multiplication of conifer embryogenic tissue that is cultured in the multiplication medium.

As used herein, the term "continuous culture," and grammatical equivalents thereof, as applied to the culture of conifer embryogenic tissue, means culturing conifer embryogenic tissue in a liquid multiplication medium by periodically (at least once) adding additional multiplication medium to the culture without removing the original multiplication medium. Thus, for example, conifer embryogenic tissue may be cultured in a volume of 50 mL multiplication medium for one week, then a further volume of 50 mL multiplication medium is added to the original volume of multiplication medium and the embryogenic tissue is further cultured in the 100 mL volume of multiplication medium. In the practice of continuous culture of conifer embryogenic tissue a small amount of the culture tissue may be removed in order to evaluate culture parameters (e.g., growth rate and tissue quality).

Unless stated otherwise, all concentration values that are expressed as percentages are weight per volume percentages.

The present invention provides methods for multiplying conifer embryogenic tissue in vitro. The methods of the present invention each includes the step of continuously culturing conifer embryogenic tissue in liquid multiplication medium for a period of time sufficient for the embryogenic tissue to multiply. The methods of the present invention can be used to multiply conifer embryogenic tissue obtained from any conifer species, such as members of the family Pinacea, including members of the genus Pinus (e.g., Loblolly pine (*Pinus taeda*)), or such as members of the genus *Pseudotsuga* (e.g., Douglas fir (*Pseudotsuga menziesii*)).

The continuous culture methods of the present invention are an improvement over the "batch" culture methods taught by the prior art. In the practice of a batch culture method, conifer embryogenic tissue is cultured in liquid multiplication medium for a period of time, the embryogenic tissue is separated from the multiplication medium (e.g., by allowing the embryogenic tissue to settle out of the medium), then aliquots of the embryogenic tissue are removed and introduced into separate volumes of fresh multiplication medium for further culture. This process is repeated as often as desired to yield a multiplicity of containers that each includes separate batches of the embryogenic tissue culture. The use of continuous culture provides several advantages over the use of batch culture: for example, continuous culture typically requires less labor than batch culture in which the embryogenic tissue must be periodically subcultured into new growth containers; and there is typically less culture variability in continuous culture than occurs between batches of embryogenic tissue in batch culture methods.

An example of embryogenic tissue useful in the practice of the present invention is embryonal suspensor masses (ESMs). ESMs can be prepared from precotyledonary embryos removed from conifer seed. The seed are typically surface sterilized before removing the precotyledonary embryos that are then cultured on, or in, an initiation medium that permits formation of ESMs that include early stage embryos in the process of multiplication by budding and cleavage. The medium may, if desired, include hormones that stimulate multiplication of the early stage embryos. Examples of hormones that can be included in the medium are auxins (e.g., 2,4-dichlorophenoxyacetic acid (2,4-D)) and cytokinins (e.g., 6-benzylaminopurine (BAP)). Auxins can be utilized, for example, at a concentration of from 1 mg/L to 200 mg/L. Cytokinins can be utilized, for example, at a concentration of from 0.1 mg/L to 50 mg/L. An example of a medium useful for culturing Loblolly pine precotyledonary embryos to induce formation of ESMs is medium $LM_1$ set forth in Example 2 herein. An example of a medium useful for culturing Douglas fir precotyledonary embryos to induce formation of ESMs is medium $DM_1$ set forth in Example 3 herein.

The multiplication medium is formulated to promote the growth and multiplication of conifer embryogenic tissue, such as embryonal suspensor masses. The multiplication medium may be agitated to promote growth and multiplication of the embryogenic tissue. The osmolality of the multiplication medium is typically in the range of 180-400 mM/kg. The multiplication medium contains nutrients that sustain the embryogenic tissue, and may include hormones, such as one or more auxins and/or cytokinins, that promote cell division and growth of the embryogenic tissue.

It is generally desirable, though not essential, to include maltose as the sole, or principal, metabolizable sugar source in the multiplication medium. Examples of useful maltose concentrations are within the range of from about 2.5% to about 6.0%. An example of a suitable Loblolly pine liquid multiplication medium is medium $LM_2$ (without gellant) set forth in Example 2 herein. An example of a suitable Douglas fir multiplication medium is medium $DM_2$ set forth in Example 3 herein. Conifer embryogenic tissue is typically cultured in a multiplication medium (e.g., for a period of up to 6 months) with periodic (e.g., once per week) addition of more multiplication medium, at a suitable temperature, such as from 10° C. to 30° C., or such as from 15° C. to 25° C., or such as from 20° C. to 23° C.

In some embodiments of the methods of the present invention, the ratio of the volume of conifer embryogenic tissue to the volume of fresh multiplication medium that is periodically added to the continuous culture of embryogenic tissue is from about 1:2 to about 1:5; in some embodiments of the methods of the present invention, the ratio of the volume of conifer embryogenic tissue to the volume of fresh multiplication medium that is periodically added to the continuous culture of embryogenic tissue is from about 1:3 to about 1:5; in some embodiments of the methods of the present invention, the ratio of the volume of conifer embryogenic tissue to the volume of fresh multiplication medium that is periodically added to the continuous culture of embryogenic tissue is from about 1:4 to about 1:5. The term "about" as used in this context includes the exact range of ratios (e.g., the range "from about 1:4 to about 1:5" includes the range from 1:4 to 1:5).

The volume of conifer embryogenic tissue can be measured by placing the culture vessel on a horizontal surface (e.g., laboratory bench) for 30 minutes at room temperature (typically in the range of 20° C. to 25° C.). The tissue settles to the bottom of the culture vessel and the volume of settled tissue is measured (e.g., by drawing the settled tissue up into a calibrated pipette, or by looking at the level of the settled tissue in relation to volume calibration marks on the culture vessel). The tissue volume measured in this way is referred to as the settled cell volume (abbreviated as SCV).

Thus, by way of representative example, conifer embryonal suspensor masses, having a settled cell volume of 10 mL, are cultured in an initial volume of 40 mL of multiplication medium for one week. The ESMs multiply and have a settled cell volume of 20 mL at the beginning of the second week. At the beginning of the second week an additional volume of multiplication medium in the range of from 40 mL to 100 mL is added to the initial volume of multiplication medium, and the ESMs are further cultured therein.

While not wishing to be bound by theory, the present inventors hypothesize that the combination of growth-promoting chemicals produced by the conifer embryogenic tissue during culture, together with the periodic addition of fresh multiplication medium, promotes multiplication of conifer embryogenic tissue. The inventors hypothesize that in batch culture the growth promoting chemicals are substantially removed or diluted when the embryogenic tissue is periodically subcultured into separate batches of fresh multiplication medium.

In some embodiments, the present invention provides methods for producing Douglas fir cotyledonary somatic embryos or Loblolly pine cotyledonary somatic embryos, wherein these methods each include the steps of: (a) culturing Douglas fir zygotic embryos, or Loblolly pine zygotic embryos, in, or on, an initiation medium for a period of time sufficient to produce embryonal suspensor masses; (b) continuously culturing the embryonal suspensor masses in liquid multiplication medium for a period of time sufficient for the embryonal suspensor masses to multiply; and (c) culturing the multiplied embryonal suspensor masses in, or on, a development medium for a period of time sufficient to produce Douglas fir, or Loblolly pine, cotyledonary somatic embryos from the embryonal suspensor masses.

The initiation medium typically includes inorganic salts and organic nutrient materials. The osmolality of the initiation medium is typically about 160 mg/kg or even lower, but it may be as high as 170 mM/kg. The initiation medium typically includes growth hormones. Examples of hormones that can be included in the initiation medium are auxins (e.g., 2,4-dichlorophenoxyacetic acid (2,4-D)) and cytokinins (e.g., 6-benzylaminopurine (BAP)). Auxins can be utilized, for example, at a concentration of from 1 mg/L to 200 mg/L. Cytokinins can be utilized, for example, at a concentration of from 0.1 mg/L to 50 mg/L.

The initiation medium may contain an adsorbent composition, especially when very high levels of growth hormones are used. The adsorbent composition can be any composition that is not toxic to the embryogenic cells at the concentrations utilized in the practice of the present methods, and that is capable of adsorbing growth-promoting hormones, and toxic compounds produced by the plant cells during pre-cotyledonary embryo development, that are present in the medium. Non-limiting examples of useful adsorbent compositions include activated charcoal, soluble poly(vinyl pyrrolidone), insoluble poly(vinyl pyrrolidone), activated alumina, and silica gel. The adsorbent composition may be present in an amount, for example, of from about 0.1 g/L to about 5 g/L. An example of a Loblolly pine initiation medium is medium $LM_1$ set forth in Example 2 herein. An example of a Douglas fir initiation medium is medium $DM_1$ set forth in Example 3 herein.

Conifer somatic cells are typically cultured in, or on, an initiation medium for a period of from 6 weeks to 12 weeks, such as from 8 weeks to 10 weeks, or such as about 8 weeks, at a temperature of from 10° C. to 30° C., such as from 15° C. to 25° C., or such as from 20° C. to 23° C.

The embryogenic tissue is transferred from the initiation medium to a multiplication medium. The composition and properties of representative multiplication media useful in the practice of the present invention are described supra.

The embryogenic tissue is then transferred from the multiplication medium to a development medium formulated to promote development of cotyledonary conifer somatic embryos from the conifer embryogenic tissue. The development medium may be a solid medium (solidified by dissolving a gellant in a liquid development medium) or a liquid medium. When a liquid development medium is used, the embryogenic tissue may be completely immersed in the medium, which may be agitated during the time that the embryogenic tissue is cultured therein. An absorbent substrate (e.g., a pad made from cellulose, or some other material that absorbs aqueous solutions, such as a development medium) may be soaked in liquid development medium, and the conifer somatic embryos disposed on the soaked pads and in contact with the development medium.

When a solid medium is used, the embryogenic tissue may be placed on the surface of the development medium, and may partially penetrate the surface of the solid medium. Thus, solid development media include media that are partially solidified and permit the embryogenic tissue to substantially penetrate into the body of the medium, and also include fully solidified media that do not permit the embryogenic tissue to penetrate the body of the solidified medium. Liquid media can be completely or partially solidified by addition of an appropriate amount of a gellant, such as agar.

The development medium contains nutrients that sustain the embryogenic tissue. Maltose may be included in the medium as the principal or sole source of metabolizable sugar for the embryogenic tissue. Useful maltose concentrations are within the range of from 2.5% to 6.0%. Suitable development media typically do not include growth-promoting hormones, such as auxins and cytokinins, but may include the hormone abscisic acid. When abscisic acid is utilized in the development medium, it is typically utilized at a concentration in the range of from 1 mg/L to 200 mg/L, such as from 1 mg/L to 100 mg/L. The osmolality of the development medium can be adjusted to a value that falls within a desired range, such as from 250 mM/Kg to 450 mM/Kg, or such as from 250 mM/Kg to 350 mM/Kg. The pH of the development medium may also be adjusted to a value within a desired range, such as from 4.5 to 6.5, or such as from 5.0 to 6.0. The embryogenic tissue is typically incubated in, or on, the development medium at a temperature in the range of from 20° C. to 24° C., such as from 21° C. to 24° C. An example of a suitable Loblolly pine development medium is medium $LM_5$ set forth in Example 2 herein. An example of a suitable Douglas fir development medium is medium $DM_4$ set forth in Example 3 herein.

Embryogenic conifer tissue is cultured in, or on, a development medium for a period of time sufficient to produce cotyledonary conifer somatic embryos from the embryogenic conifer tissue. For example, Douglas fir embryonal suspensor masses are typically cultured in, or on, development medium for from about seven weeks to about eight weeks to produce Douglas fir cotyledonary somatic embryos. Again by way of example, Loblolly pine embryonal suspensor masses are typically cultured in, or on, development medium for from about ten weeks to about 12 weeks to produce Loblolly pine cotyledonary somatic embryos.

The cotyledonary conifer somatic embryos produced using the methods of the invention can optionally be germinated to form conifer plants which can be grown into conifer trees, if desired. The germinated plants can be transferred to soil for further growth. For example, the germinated plants can be planted in soil in a greenhouse and allowed to grow before being transplanted to an outdoor site. Typically, the cotyledonary conifer somatic embryos are illuminated to stimulate germination. Typically, all the steps of the methods of the invention, except germination, are conducted in the dark.

The cotyledonary conifer somatic embryos produced using the methods of the invention can also be introduced into manufactured seeds which may be stored for subsequent planting and germination, or which may be planted without a period of storage. Representative examples of useful manufactured seeds include the manufactured seeds disclosed in U.S. Pat. No. 5,687,504, which is incorporated by reference herein in its entirety.

The methods of the invention can be used, for example, to produce clones of individual conifer trees that possess one or more desirable characteristics, such as a rapid growth rate. Thus, in one aspect, the present invention provides methods for producing a population of genetically-identical, cotyledonary, conifer somatic embryos, wherein any of the methods described herein is used to produce a population of genetically-identical, cotyledonary, conifer somatic embryos from a genetically homogeneous starting material (e.g., from a single Loblolly pine or Douglas fir zygotic embryo).

The following examples merely illustrate the best mode now contemplated for practicing the invention, but should not be construed to limit the invention.

EXAMPLE 1

This Example demonstrates the successful use of continuous culture in the multiplication stage of Loblolly pine somatic embryo production.

Materials and Methods: Loblolly pine genotypes A, B, and C were used in Treatments 1-5 (described below). Loblolly pine genotype A was used in Treatment 6 (described below). ESMs were continuously cultured in multiplication medium in flasks for six weeks. The composition of the multiplication medium is shown in Table 1 below.

TABLE 1

Loblolly Pine Multiplication Medium (LM medium)

| | mg/L |
|---|---|
| Salts | |
| $NH_4NO_3$ | 150 |
| $KNO_3$ | 909.9 |
| $Ca(NO_3)_2 \cdot 2H_2O$ | 236.15 |
| $MgSO_4 \cdot 7H_2O$ | 246.5 |
| $Mg(NO_3)_2 \cdot 6H_2O$ | 256.5 |
| $MgCl_2 \cdot 6H_2O$ | 50 |
| $KH_2PO_4$ | 136 |
| $CaCl_2 \cdot 6H_2O$ | 50 |
| KI | 4.15 |
| $H_3BO_3$ | 15.5 |
| $MnSO_4 \cdot H_2O$ | 10.5 |
| $ZnSO_4 \cdot 7H_2O$ | 14.4 |
| $NaMoO_4 \cdot 2H_2O$ | 0.125 |
| $CuSO_4 \cdot 5H_2O$ | 0.125 |
| $CoCl_2 \, 6H_2O$ | 0.125 |
| $FeSO_4 \cdot 7H_2O$ | 27.87 |
| $Na_2EDTA$ | 37.26 |
| Vitamins/Amino Acids | |
| Nicotinic Acid | 0.5 |
| Pyridoxine HCl | 0.5 |
| Thiamine HCl | 1 |
| Glycine | 2 |
| Sugar/Agar | |
| Myo-Inositol | 200 |
| Casein hydrolysate | 500 |
| L-glutamine | 1000 |
| Maltose | 30000 |
| Hormones | |
| 2,4-D | 1.1 |
| BAP | 0.1 |
| Kinetin | 0.1 |

The following multiplication culture conditions were used.

Treatment 1 (batch culture control): 10 mL of ESM was inoculated into 40 mL multiplication medium in a 250 mL flask. Once each week 10 mL of settled cell volume (SCV) of ESM was transferred into 40 mL of fresh LM medium. The ratio of SCV to fresh medium was maintained at 1:4. The ratio of SCV to total volume of medium (plus ESM) was maintained at 1:5.

Treatment 2: 10 mL of ESM was inoculated into 40 mL multiplication medium in a 250 mL flask. After one week fresh LM medium was added to the flask. It was assumed that the amount of SCV had doubled from the previous week. Sufficient fresh LM medium was added to the flask so that the ratio of SCV to fresh medium was estimated to be 1:2. The ratio of SCV to total volume of medium was maintained at 1:5. Treatment 2 was designed to "starve" the ESM to verify that the ESM turns brown when too little fresh LM medium is provided.

Treatment 3: 10 mL of ESM was inoculated into 40 mL multiplication medium in a 250 mL flask. After one week fresh LM medium was added to the flask. It was assumed that the amount of SCV had doubled from the previous week. It was also assumed that there was less old LM medium in the flask at the end of the first week, than at the beginning of the first week, because the ESM had used some of the old medium to grow. Sufficient fresh LM medium was therefore added to ensure that the ratio of SCV to total volume of medium was maintained at 1:5. The ratio of SCV to fresh medium was intended to be 1:2.5. Like Treatment 2, Treatment 3 was designed to "starve" the ESM to verify that the ESM turns brown when too little fresh LM medium is provided.

Treatment 4: 10 mL of ESM was inoculated into 40 mL multiplication medium in a 250 mL flask. After one week fresh LM medium was added to the flask. It was assumed that the amount of SCV had doubled from the previous week, and the estimated volume of SCV was multiplied by 4 to obtain the volume of fresh LM medium to add. Old LM medium was not considered in the calculation. Thus, the ratio of SCV to fresh LM medium was intended to be 1:4. The ratio of SCV to total volume of medium was not controlled. Treatment 4 was designed to supply enough fresh LM medium, by estimation, to promote further growth of the ESM, assuming that the ESM doubles weekly and that the cells need enough an amount of fresh medium that equals 4 times the SCV.

Treatment 5: 10 mL of ESM was inoculated into 40 mL multiplication medium in a 250 mL flask. After one week fresh LM medium was added to the flask. The volume of SCV was measured as it was transferred to a new empty flask. The volume of the old medium was also measured and transferred to the same new flask as the SCV. The volume of SCV was multiplied by 4 to determine the volume of fresh LM medium to add. The ratio of SCV to fresh LM medium was maintained at 1:4. The ratio of SCV to total volume of medium was not controlled. Like Treatment 4, Treatment 5 was designed to supply enough fresh LM medium to promote further growth of the ESM. In Treatment 5, the volume of SCV was actually measured, rather than estimating the volume as in Treatment 4.

Treatment 6: 20 mL of genotype A ESM was used to start a culture in a continuous culture container. The continuous culture container was an Optima 6 liter culture system sold by MetaBios Inc., 135 Innovation & Development Center, University of Victoria, R-Hut McKenzie Avenue, Victoria, BC Canada, V8W 3W2. Each week the volume of SCV was visually estimated, and fresh LM medium was pumped into the vessel using a sterile hose and a connector. Samples of ESM were collected from the vessel each week using a sterile syringe and tubing. The ratio of SCV to fresh LM medium was intended to be 1:4. The ratio of SCV to total volume of medium was not controlled. Treatment 6 was a scaled-up version of Treatment 4 using a continuous culture vessel.

Table 2 shows the estimated and measured volumes (in milliliters (mL)) of LM medium, the ratio of SCV to fresh LM medium volume (abbreviated as Ratio SCV:fresh), and the ratio of SCV to total medium volume (abbreviated as Ratio SCV:total) for each of the six treatments.

TABLE 2

| | volumes estimated | | | | volumes measured | | | vol. estimated |
|---|---|---|---|---|---|---|---|---|
| | Trt #1 | Trt #2 | Trt #3 | Trt #4 | Trt #5 Genotype A | Trt #5 Genotype B | Trt #5 Genotype C | Trt #6 Genotype A |
| | volumes estimated | | | | volumes measured | | | |
| Week 0 | | | | | | | | |
| SCV | 10 | 10 | 10 | 10 | 10 | 10 | 10 | 20 |
| Old Media | | | | | | | | |
| Fresh Media | 40 | 40 | 40 | 40 | 40 | 40 | 40 | 80 |
| Total | 50 | 50 | 50 | 50 | 50 | 50 | 50 | 100 |
| ratio SCV:total | 0.2 | 0.2 | 0.2 | 0.2 | 0.2 | 0.2 | 0.2 | 0.2 |
| Ratio SCV:fresh | 0.25 | 0.25 | 0.25 | 0.25 | 0.25 | 0.25 | 0.25 | 0.5 |
| Week 1 | | | | | | | | |
| SCV | 10 | 20 | 20 | 20 | 20 | 21 | 12.5 | 40 |
| Old Media | 0 | 40 | 30 | 30 | 26 | 23 | 33.5 | 80 |
| Fresh Media | 40 | 40 | 50 | 80 | 80 | 84 | 50 | 160 |
| Total | 50 | 100 | 100 | 130 | 126 | 128 | 96 | 280 |
| ratio SCV:total | 0.20 | 0.20 | 0.20 | 0.15 | 0.16 | 0.16 | 0.13 | 0.14 |
| Ratio SCV:fresh | 0.25 | 0.50 | 0.40 | 0.25 | 0.25 | 0.25 | 0.25 | 0.25 |
| Week 2 | | | | | | | | |
| SCV | 10 | 40 | 40 | 40 | 39 | 38 | 16 | 80 |
| Old Media | | 80 | 60 | 90 | 88 | 88 | 73 | 240 |
| Fresh Media | 40 | 80 | 100 | 160 | 156 | 152 | 64 | 320 |
| Total | 50 | 200 | 200 | 290 | 283 | 278 | 153 | 640 |
| ratio SCV:total | 0.20 | 0.20 | 0.20 | 0.14 | 0.14 | 0.14 | 0.10 | 0.13 |
| Ratio SCV:fresh | 0.25 | 0.50 | 0.40 | 0.25 | 0.25 | 0.25 | 0.25 | 0.25 |
| | | subsampling begins | | | subsampling begins | | | |
| Week 3 | | | | | | | | |
| SCV | 10 | 80 | 80 | 80 | 30 | 30 | 30 | 160 |
| Old Media | 0 | 160 | 120 | 210 | 58 | 60 | 120 | 480 |
| Fresh Media | 40 | 160 | 200 | 320 | 120 | 120 | 120 | 640 |
| Total | 50 | 400 | 400 | 610 | 208 | 210 | 270 | 1280 |
| ratio SCV:total | 0.20 | 0.20 | 0.20 | 0.13 | 0.14 | 0.14 | 0.11 | 0.13 |
| Ratio SCV:fresh | 0.25 | 0.50 | 0.40 | 0.25 | 0.25 | 0.25 | 0.25 | 0.25 |
| Week 4 | | | | | | | | |
| SCV | 10 | 160 | 160 | 160 | 30 | 30 | 30 | 320 |
| Old Media | 0 | 320 | 240 | 450 | 49 | 33 | no data | 960 |
| Fresh Media | 40 | 320 | 400 | 640 | 120 | 120 | 120 | 1280 |
| Total | 50 | 800 | 800 | 1250 | 199 | 183 | 150 | 2560 |
| ratio SCV:total | 0.20 | 0.20 | 0.20 | 0.13 | 0.15 | 0.16 | | 0.13 |
| Ratio SCV:fresh | 0.25 | 0.50 | 0.40 | 0.25 | 0.25 | 0.25 | 0.25 | 0.25 |
| Week 5 | | | | | | | | |
| SCV | 10 | 320 | 320 | 320 | 30 | 30 | 25 | 640 |
| Old Media | 0 | 640 | 480 | 900 | 119 | 50 | 82 | 960 |
| Fresh Media | 40 | 640 | 800 | 1280 | 120 | 120 | 100 | 2560 |
| Total | 50 | 1600 | 1600 | 2500 | 269 | 200 | 207 | 4160 |
| ratio SCV:total | 0.20 | 0.20 | 0.20 | 0.13 | 0.11 | 0.15 | 0.12 | 0.15 |
| Ratio SCV:fresh | 0.25 | 0.50 | 0.40 | 0.25 | 0.25 | 0.25 | 0.25 | 0.25 |

An additional genotype B culture was conducted in a continuous culture vessel. 40 ml of genotype B ESM were inoculated into 200 ml of fresh LM medium in a continuous culture vessel on Week 0. Each week fresh LM medium was added as described in connection with Treatment 6. It was assumed that the SCV doubled each week, and the estimated SCV was multiplied by 4 to determine the volume of fresh LM medium to add. Old LM media was not considered in the calculation. The ratio of SCV to the volume of fresh LM medium was intended to be 1:4. The ratio of SCV to total volume of LM medium was not controlled. This trial continued for five weeks. A batch culture control flask was also maintained that was identical to Treatment 1 described above.

Culture Methodology: All cultures were started in small (250 mL) flasks, but by the end of the first week the volumes had grown substantially. The cultures were switched to 500 mL flasks. By the end of the second week Treatments 2 though 6 were being maintained in 1 liter flasks, with anywhere between 200 mL and 350 mL of culture per flask. Treatment 1 was always kept in a 250 mL flask.

During weeks 3, 4, and 5, the volumes of SCV and media multiplied rapidly. To avoid maintaining several large flasks for each treatment/genotype combination, sub-samples of ESM and old media were removed, transferred to a new flask, and then added to the appropriate amount of fresh LM medium in the new flask. The ESM and the old medium were completely mixed together before sub-sampling the mixture for Treatments 2 through 4. For Treatment 5 the flasks were settled and then the SCV and the old media was measured separately using a 30 mL, glass, wide-bore pipette. The existing ratio of SCV to old media was calculated. SCV and old media were then transferred to a new flask in the same proportion. This kept the number of flasks down to one large flask per genotype/treatment combination, or a total of 15 flasks.

Data collection: At each weekly culture transfer, 2 mL to 3 mL of SCV was sampled to assess the quality of the embryos. For the first week, 3 mL of the combined ESM plus old media mixture were withdrawn. This amount of the mixture was insufficient to provide enough ESMs to assess embryo quality. For the remaining weeks, 2 mL to 3 mL of SCV were withdrawn and saved for culture assessment. This practice may have slightly changed the ratio of SCV to old medium, but the significance of this discrepancy decreased as the contents of the flasks increased in volume over time.

Results: Treatments 1, 2, and 3 maintained the ratio of SCV to total medium volume at 1:5. This is a ratio that has worked well in the past with batch cultures of Loblolly pine ESMs. Treatments 4, 5, and 6 added an amount of fresh medium that was 4 times the SCV without regard to the total volume. As shown in Table 2, all treatments in which fresh LM medium was added in an amount that was 4 times the estimated SCV volume exceeded the SCV to multiplication medium ratio of 1:5 that has been used in batch cultures. Nonetheless, ESM still grew faster under these conditions in continuous culture than it did when maintained at a ratio of 1:5 SCV to total medium volume in batch cultures.

With respect to ESM quality, it was noted that ESM in Treatment 2 became stressed and small during the final weeks, whereas Treatments 4 and 5, which received a much larger proportion of fresh multiplication medium, generally showed much better embryo quality. The early stage embryo quality of the ESM in continuous culture was superior to that of the batch culture in the flasks; in general, the embryos in continuous culture were more synchronized, with smaller, more organized heads and directional suspensors, that the embryos in batch culture.

With respect to the growth of ESMs in the various culture conditions, Table 3 shows the volume of ESM obtained from Treatments 1 and 5 for each of genotypes A, B, and C. These calculations were done by adding back the volume of ESM discarded each week and applying the observed growth rate to derive a total extrapolated volume. Beginning after the second week in culture, Treatment 5 (continuous culture flasks) grew much faster than Treatment 1 (batch culture) for all three genotypes.

TABLE 3

Extrapolated settled cell volumes (mL) for Treatments 1 and 5.

| | Week | | | | | | |
|---|---|---|---|---|---|---|---|
| | 0 | 1 | 2 | 3 | 4 | 5 | 6 |
| A.1 | 10 | 16 | 35 | 67 | 127 | 292 | 380 |
| A.5 | 10 | 20 | 39 | 93 | 158 | 248 | 614 |
| B.1 | 10 | 15 | 29 | 48 | 97 | 165 | 329 |
| B.5 | 10 | 21 | 38 | 90 | 270 | 540 | 1134 |
| C.1 | 10 | 13 | 18 | 27 | 35 | 42 | 42 |
| C.5 | 10 | 13 | 16 | 35 | 56 | 108 | 130 |

Genotypes A and B showed better early stage embryo quality in Treatments 4 and 5. Genotype A was initially stressed in Treatments 2 and 3, until the cultures adjusted to the culture conditions. In the later weeks both genotypes no longer showed stress, but the embryos were less synchronized in Treatments 2 and 3 than they were in Treatments 4 and 5. These generally fast-growing genotypes may have been limited by nutrients in Treatments 2 and 3.

In all genotypes, the early stage embryos in Treatments 4 and 5 appeared to be most synchronized. In Treatment 4 it was assumed that the SCV doubled weekly, and sufficient fresh medium was added to maintain a ratio of 1 part SCV to 4 parts fresh medium. Both Treatment 4, in which the 1:4 ratio of SCV to fresh LM medium was based on an estimate of the SCV volume, and Treatment 5, in which the 1:4 ratio of SCV to fresh LM medium was based on an actual measurement of the SCV volume, produced high quality ESMs. Consequently, estimating a doubling of SCV each week and adding enough fresh multiplication medium to maintain a 1:4 ratio of SCV to fresh multiplication medium is a relatively straightforward method for growing liquid Loblolly pine ESM cultures in continuous culture.

All the genotype A ESM inoculated into both the continuous culture vessel and the flasks came from the same culture. After the first week of culture the ESM appeared similar, in both the continuous culture vessel and the flasks. By weeks 2 and 3, the ESM in the flasks appeared healthier than the ESM in the continuous culture vessel. During weeks 4, 5, and 6, however, the ESM in the continuous culture vessel appeared to be at least as healthy as the ESM in the flasks. The results of this experiment showed that, after a two to three week period of adjustment, Loblolly pine ESMs multiplied in continuous culture vessels were as good as, or better than, those multiplied in flasks at similar ratios of SCV to fresh medium.

EXAMPLE 2

This example describes a representative method of the present invention for producing Loblolly pine cotyledonary somatic embryos.

The composition of the basal tissue culture medium is set forth in Table 4. The modifications to the basal medium composition that are required for each culture medium are listed in Table 5. Each tissue culture medium is prepared by mixing together all the ingredients, with the exception of abscisic acid and maltose (if needed), and bringing the medium to the desired volume prior to autoclaving (15 minutes at 121° C., 15 psi). The abscisic acid is filter-sterilized and aseptically added to the sterile medium. L-glutamine is also filter-sterilized prior to addition to maintenance medium. In media requiring maltose, the medium is made up to 90% of the required volume. A 10× stock solution of maltose is autoclaved, or filter-sterilized, and added to the autoclaved medium. Gelrite is added to make solid LM-1 medium. Ten ml of LM-1 medium is poured into 60×15 mm plates, or 20 ml of LM-1 medium is poured into 100×25 mm plates.

TABLE 4

LOBLOLLY PINE BASAL CULTURE MEDIUM (LM)

| Basal Salts | mg/L | Basal Salts | mg/L |
|---|---|---|---|
| $NH_4NO_3$ | 150 | $H_3BO_3$ | 15.5 |
| $KNO_3$ | 909.9 | $MnSO_4 \cdot H_2O$ | 10.5 |
| $Ca(NO_3)_2 \cdot 4H_2O$ | 236.2 | $ZnSO_4 \cdot 7H_2O$ | 14.4 |
| $MgSO_4 \cdot 7H_2O$ | 246.5 | $NaMoO_4 \cdot 2H_2O$ | 0.125 |
| $Mg(NO_3)_2 \cdot 6H_2O$ | 256.5 | $CuSO_4 \cdot 5H_2O$ | 0.125 |
| $MgCl_2 \cdot 6H_2O$ | 50 | $CoCl_2 \, 6H_2O$ | 0.125 |
| $KH_2PO_4$ | 136 | $FeSO_4 \cdot 7H_2O$ | 27.85 |
| $CaCl_2 \cdot 2H_2O$ | 50 | $Na_2EDTA$ | 37.25 |
| KI | 4.15 | | |
| Organic Additives | mg/L | Organic Additives | mg/L |
| Nicotinic acid | 0.5 | Casamino acids | 500 |
| Pyridoxine·HCl | 0.5 | L-Glutamine* | varies |
| Thiamine·HCl | 1 | Myo-Inositol | varies |
| Glycine | 2 | Carbohydrate | varies |
| pH | 5.7 | | |

*L-glutamine is filter sterilized in multiplication medium for some genotypes.

(middle of July). The optimal embryo stage for initiation is when the apical dome begins to develop.

The seeds are removed from the cones and are immersed in a 10% solution of Liquinox that includes a few drops of Tween-20 detergent, and agitated for 10 minutes. The seeds are then rinsed with distilled water for 30 minutes. The seeds are agitated in a 15% (v/v) solution of $H_2O_2$ for 10 minutes. The seeds are then washed five times by agitating in successive aliquots of sterile water in a laminar-flow hood.

The surface-sterilized seeds are then transferred to a petri plate, and the seeds are viewed under a dissecting microscope, and the seed coat and nucellar membrane are removed with scalpel and forceps. The excised female gametophyte is placed onto LM-1 induction medium. The excised gametophyte should be placed so that its longitudinal axis is parallel to the media surface, and so that the micropyle is in contact with, but not submerged in, the culture medium. The plates are sealed with a double layer of parafilm and the cultures are incubated in the dark at 23° C.

After 2-3 weeks, extrusion of somatic embryos occurs from the micropylar end of the female gametophyte. A mucilaginous, translucent-white mass develops (0.5-10 mm) around the heads of these immature embryos. This is called an embryonal suspensor mass (ESM). An embryonal suspensor mass is made up of embryos at various early stages of development. Each embryo contains an embryonal head and suspensor system.

Multiplication of Embryonal Suspensor Masses: 5-6 weeks after placing the excised female gametophytes on LM-1 induction medium, the ESM is separated from the original explants and transferred onto solid multiplication medium (LM-2). ESM cultures multiply by natural conifer-type cleavage polyembryony. ESM cultures are subcultured

TABLE 5

FORMULATIONS OF LOBLOLLY PINE MEDIA

| (All units are in mg/L) | LM-1 Stage I Initiation | LM-2 Stage II Multiplication | LM-3 Stage II Rinse | LM-4 Stage III Solid Develpmt | LM-5 Stage III Liquid Develpmt | LM-6* Stage IV Stratification |
|---|---|---|---|---|---|---|
| L-Proline | — | — | 100 | 100 | 100 | 100 |
| L-Asparagine | — | — | 100 | 100 | 100 | 100 |
| L-Arginine | — | — | 50 | 50 | 50 | 50 |
| L-Alanine | — | — | 20 | 20 | 20 | 20 |
| L-Serine | — | — | 20 | 20 | 20 | 20 |
| L-glutamine | 250 | 1000 | 1000 | 1000 | 1000 | 1000 |
| Myo-Inositol | 200 | 200 | 1000 | 1000 | 1000 | 1000 |
| Maltose | 30,000 | 30,000 | 25,000 | 25,000 | 25,000 | 25,000 |
| Glucose | — | — | — | 10,000 | 10,000 | — |
| PEG 8000 | — | — | — | 100,000 | 120,000 | — |
| Activated charcoal | 1250 | — | — | 1000 | 1000 | 1000 |
| Gelrite | 1600 | 1600** | — | 2500 | — | — |
| 2,4-D | 55 | 1.1 | — | — | — | — |
| BAP | 7.5 | 0.1 | — | — | — | — |
| Kinetin | 7.5 | 0.1 | — | — | — | — |
| ABA | — | +/−1.0*** | 10 | 25 | 25 | — |

*LM-6 Stratification medium has only half the basal amounts of $FeSO_4 \cdot 7H_2O$ (13.93 mg/L) and $Na_2EDTA$ (18.83 mg/L).
**Gelrite is not added to liquid multiplication medium
***ABA is added on a per-genotype basis..
The pH of all media are adjusted to 5.7.

Initiation of Embryogenic Cultures: Female cones are collected when immature embryos reach pre-dome or dome stage in development. Collection usually begins in the first week of July (about 4-6 weeks after fertilization), and continues until the first appearance of cotyledon primordia every two weeks onto fresh medium and incubated in the dark at 23° C. The ESM cultures are divided into two pieces when they reach 1 cm long, and all the pieces are maintained until there are several which can be used to start a suspension culture.

Establishing Liquid Multiplication Cultures: 1-2 grams (fresh weight) ESM (four or five 1-cm pieces) are transferred into a 250 ml Erlenmeyer flask containing 20 ml of LM-2 liquid medium. The flask is placed on a rotary shaker (90-110 rpm) in darkness at 23° C. After one week the settled cell volume (SCV) is measured, and if the SCV is less than 3 ml, the flask is returned to the shaker without making any additions or changes to the medium. If the SCV is at least 5 ml, 25 ml of fresh medium are added to the flask, which is returned to the shaker.

After the second week, the cultures are settled for 15 minutes on a tilted flask holder. If the flask did not have medium added the week before, 10 ml of spent media are removed and replaced with 10 ml of fresh medium. If medium was added to the flask in the previous week, and the culture appears to be growing vigorously, the culture is handled as follows. When cultures are sufficiently established to produce 10 ml, or more, of settled cells per week, the ESM is transferred to a continuous culture vessel and a volume of media added such that the ratio of ESM to fresh multiplication medium is 1:4. The continuous culture is augmented with weekly additions of fresh LM-2 liquid medium, without subculture. The vessel is settled for 15 minutes, the volume of ESM estimated, and fresh medium added at a ratio of 1:4 cells to fresh medium (v/v). The old medium is left in the culture vessel and is not considered in the volume calculation. Cultures at this stage may be continuously multiplied, cryostored, or they may be singulated and developed for germination.

Embryo Development: Embryo development is completed using a liquid development medium, LM-5, that is soaked into a double layer of Concert 10% CC pads in a petri dish or Cambro box. The cultures are settled after culture in maintenance medium, and aspirated to remove the supernatant. The settled cell volume is measured with a pipette during transfer to a cytostir beaker. A volume of rinse medium (LM-3), equal to the settled cell volume, is added to the settled cells. The cells in LM-3 medium are swirled in the cytostir beaker, and settled for an additional 10 minutes. Half the supernatant is removed, and the remaining ESM are transferred to a cytostir beaker. The cells are stirred on a stir plate.

The ESM is pipetted onto a filter paper that is located on a pad soaked in liquid medium. 0.75 ml ESM mixture is used per standard 2"×2" pad. The plates are sealed with two layers of parafilm, and incubated in the dark at 23° C. After about 12 weeks the ESM cultures produce cotyledonary embryos.

Stratification: Stratification is the process of placing embryos in a cold moist environment for several weeks, which is thought to simulate winter.

Plates are prepared that include a single layer of pad material (2"×2" 10% CC, or larger cut to fit Cambro boxes). About 18-19 ml liquid LM-6 media are added per 2"×2" pad (more for boxes). A filter paper bearing the Loblolly pine embryos is transferred from development plates to pads of stratification medium. Alternatively, zygotic-like cotyledonary embryos may be selected from the development medium and placed onto new filter papers on stratification medium. Plates are sealed with parafilm and placed in the dark at 2-6° C. for four weeks.

Conditioning Somatic Embryos: In addition to stratification, a post-development conditioning treatment, in which embryos are exposed to a high relative humidity (RH) environment, improves germination. The high RH environment is provided by the addition of sterile water to a half-Cambro box. Embryos are singulated after stratification and placed onto dry filter papers in a large petri plate. The open plate is placed in the half-Cambro box containing sterile water. The embryos are exposed to the high RH environment until the moisture contents of the embryos reach 60-65%. The boxes are closed so that the gaskets seal tightly, and are clipped shut with binder clips before being placed in the dark for three weeks at 23° C. After conditioning, the mature somatic embryos are removed from the boxes and can be inserted into manufactured seed for subsequent germination and seedling establishment, or can be directly germinated.

EXAMPLE 3

This example describes a representative method of the present invention for producing Douglas fir (*Pseudotsuga menziesii*) cotyledonary somatic embryos.

The composition of basal medium is listed in Table 6. Modifications of the basal medium required for each culture medium are listed in Table 7. The composition of stratification medium is set forth in Table 8. The concentration units in Tables 6, 7, and 8 are milligrams per liter (mg/L). The media are prepared by mixing together all of the ingredients, with the exception of abscisic acid (ABA), gibberellic acid (GA) and maltose (if needed), and bringing the media to the desired volume prior to autoclaving for 15 minutes at 121° C., 15 psi. ABA and GA 4/7 are filter-sterilized and aseptically added to sterile media. If the medium requires maltose, the medium is first brought to 90% of the desired volume, and an aliquot of a sterile, 10×, stock solution of maltose is added to the autoclaved media. Gelrite is used to make solid DM-1 plates, and tissue culture (TC) agar to make solid DM-2 plates. Ten ml/plate of DM-1 or DM-2 medium is added to 60×15 mm plates, or 20 ml/plate of DM-1 or DM-2 medium is added to 100×25 mm plates.

TABLE 6

DOUGLAS FIR BASIC CULTURE MEDIA (DM)

| Basal Salts | mg/L | Organic Additives | mg/L |
|---|---|---|---|
| $KNO_3$ | varies | Myo-Inositol | varies |
| $CaCl_2 \cdot 2H_2O$ | 200 | Thiamine·HCl | 1 |
| $Ca(NO_3)_2 \cdot 4H_2O$ | varies | Nicotinic acid | 0.5 |
| $KH_2PO_4$ | 340 | Pyridoxine·HCl | 0.5 |
| $MgSO_4 \cdot 7H_2O$ | 400 | Glycine | 2 |
| $MnSO_4 \cdot H_2O$ | 15.8 | L-Glutamine | varies |
| $ZnSO_4 \cdot 7H_2O$ | 8 | Casamino acids | 500 |
| $CuSO_4 \cdot 5H_2O$ | 0.024 | Sucrose or Maltose | varies |
| $FeSO_4 \cdot 7H_2O$ | 27.85 | pH | 5.7 |
| $Na_2EDTA$ | 37.25 | | |
| $H_3BO_3$ | 5 | | |
| $NaMoO_4 \cdot 2H_2O$ | 0.2 | | |
| $CoCl_2 \cdot 6H_2O$ | 0.02 | | |
| KI | 1 | | |

TABLE 7

FORMULATIONS OF DOUGLAS FIR MEDIA

| | DM-1 Stage I Initiation | DM-2 Stage II Multiplication | DM-3 Stage III Singulation | DM-4 Stage IV Development |
|---|---|---|---|---|
| $KNO_3$ | 1250(1) | 1250 | 1050 | 2500 |
| $Ca(NO_3)_2 \cdot 4H_2O$ | — | — | 200 | — |
| Myo-Inositol | 1000 | 5000 | 100 | 100 |
| L-Glutamine | 450 | 1000 | 1000 | 750 |
| Amino acid mixture(2) | — | — | — | 290 |
| Sucrose | 15,000 | | | |
| Maltose | | 30,000 | 20,000 | 25,000 |
| PEG 8000 | — | — | — | 190,000 |
| 2.4-D | 110 | 1.1 | — | — |

TABLE 7-continued

FORMULATIONS OF DOUGLAS FIR MEDIA

|  | DM-1 Stage I Initiation | DM-2 Stage II Multiplication | DM-3 Stage III Singulation | DM-4 Stage IV Development |
|---|---|---|---|---|
| N6-Benzyladenine (BAP) | 45 | 0.22 | — | — |
| Kinetin | 43 | 0.22 | — | — |
| Abscisic acid | — | — | 10/5/5 | 10 |
| Gibberellic acid | — | — | — | 7.5 |
| Activated charcoal | 2500 | — | — | 1000 |
| Tissue culture agar | — | 5000(3) | — | — |
| Gelrite | 1800 | — | — | — |

(1) All units are in mg/L (or ppm)
(2) L-Proline - 100, L-Asparagine - 100, L-Arginine - 50, L-Alanine - 20, L-Serine - 20
(3) Tissue culture agar not used for liquid media
The pH of all media are adjusted to 5.7

TABLE 8

STRATIFICATION MEDIUM (SM)

| Basal Salts | mg/L | Organic Additives | mg/L |
|---|---|---|---|
| $NH_4NO_3$ | 206.3 | Myo-Inositol | 100 |
| $KNO_3$ | 1170 | Thiamine·HCl | 1 |
| $CaCl_2·2H_2O$ | 220 | Nicotinic acid | 0.5 |
| $Ca(NO_3)_2·4H_2O$ | none | Pyridoxine·HCl | 0.5 |
| $KH_2PO_4$ | 85 | Glycine | 2 |
| $MgSO_4·7H_2O$ | 185 | Casamino acids | none |
| $MnSO_4·H_2O$ | 8.45 | Sucrose | 20,000 |
| $ZnSO_4·7H_2O$ | 4.3 | Activated charcoal | 2500 |
| $CuSO_4·5H_2O$ | 0.013 | pH | 5.7 |
| $FeSO_4·7H_2O$ | 13.93 | | |
| $Na_2EDTA$ | 18.63 | | |
| $H_3BO_3$ | 3.1 | | |
| $NaMoO_4·2H_2O$ | 0.125 | | |
| $CoCl_2·6H_2O$ | 0.013 | | |
| KI | 0.42 | | |

Initiation of Embryogenic Cultures: Female cones are collected when immature embryos reach pre-dome and dome stage in development. Collections usually begin in the first week of July (about 4-6 weeks after fertilization) until the first appearance of cotyledon primordia (middle of July). The optimal embryo stage for initiation is when the apical dome begins to develop, but prior to formation of cotyledons.

The seeds are removed from the cones and are immersed in a 10% solution of Liquinox that includes a few drops of Tween-20 detergent, and agitated for 10 minutes. The seeds are then rinsed with distilled water for 30 minutes. The seeds are agitated in a 20% (v/v) solution of $H_2O_2$ for 10 minutes. The seeds are then washed five times by agitating in successive aliquots of sterile water in a laminar-flow hood.

The surface-sterilized seeds are then transferred to a petri plate, and the seeds are viewed under a dissecting microscope, and the embryos are excised so that they remain attached to the female gametophyte. The excised female gametophyte is placed onto DM-1 induction medium so that the embryos are touching the medium. The plates are wrapped with a double layer of parafilm and the cultures are incubated in the dark at 23° C.

After 5-9 weeks, extrusion of somatic embryos occurs from the micropylar end of the female gametophyte. A mucilaginous, translucent-white mass develops (0.5-10 mm) around the heads of these immature embryos. This is called an embryonal suspensor mass (ESM). An embryonal suspensor mass is made up of embryos at various early stages of development. Each embryo contains an embryonal head and suspensor system.

Multiplication of Embryonal Suspensor Masses: The ESM is separated from the original explants and transferred onto solid multiplication medium (DM-2). ESM cultures multiply by natural conifer-type cleavage polyembryony. ESM cultures are subcultured every two weeks onto fresh medium and incubated in the dark at 23° C. The ESM cultures are divided into two pieces when they reach 1 cm long, and all the pieces are maintained until there are several which can be used to start a suspension culture.

Establishing Liquid Multiplication Cultures: 1-2 grams (fresh weight) ESM (four or five 1-cm pieces) are transferred into a 250 ml Erlenmeyer flask containing 20 ml of DM-2 liquid medium. The flask is placed on a rotary shaker (90-110 rpm) in darkness at 23° C. After one week 25 ml of fresh medium are added to the flask that is returned to the shaker.

After the second week, the cultures are settled for 15 minutes on a tilted flask holder. The supernatant (spent medium) is removed with an aspirating pipette, and a 5 ml broken-tip pipette is used to measure the settled cell volume (SCV). If the SCV is 2-4 ml, the SCV is returned to the flask and medium is added to achieve a 1:9 ratio of cells to medium (v/v). If the SCV is 5 ml or more, the culture is handled as follows. When cultures are sufficiently established to produce 5 ml, or more, of settled cells per week, the ESM is transferred to a continuous culture vessel and a volume of media added such that the ratio of ESM to fresh multiplication medium is 1:9. The continuous culture is augmented with weekly additions of fresh DM-2 medium, without subculture. The vessel is settled for 15 minutes, the volume of ESM estimated, and fresh medium added at a ratio of 1:9 cells to fresh medium (v/v). The old medium is left in the culture vessel and is not considered in the volume calculation. Cultures at this stage may be continuously multiplied, cryostored, or they may be singulated and developed for germination.

Somatic Embryo Singulation: Abscisic acid (ABA) is important for cotyledonary embryo development because it inhibits cleavage polyembryony and allows embryo singulation and further embryo development. ESM suspension cultures are transferred into DM-3 liquid medium containing 10.0 mg/L ABA. After one week, the cultures are subcultured again into DM-3 medium that includes 5.0 mg/L ABA. After another week the cultures are again subcultured into DM-3 medium that includes 5.0 mg/L ABA.

Embryo Development: Embryo development is completed using a liquid development medium, DM-4, that is soaked into a double layer of Concert 10% CC pads in a petri dish or Cambro box. The 2"×2" pads take 15-16 ml of media per pad. The cultures are settled after culture in singulation medium, and aspirated to remove the supernatant. The settled cell volume is measured with a pipette during transfer to a cytostir beaker. A volume of the reserved supernatant, equal to half the settled cell volume, is added to the cytostir beaker, and the culture is then stirred on a stir plate. Then 0.75 ml settled ESM mixture (approximately 100 mg ESMs) is pipetted onto the filter paper located on DM-4 media-soaked pads. The plates are sealed with two layers of Parafilm, and incubated in the dark at 23° C. After about 7-8 weeks the ESM cultures produce cotyledonary embryos.

Stratification: Stratification is the process of placing embryos in a cold moist environment for several weeks, which is thought to simulate winter.

Plates are prepared that include a single layer of pad material (2"×2" 10% CC, or larger cut to fit Cambro boxes). About 18-19 ml liquid ESM medium are added per 2"×2" pad (more for boxes). A filter paper bearing the Douglas fir embryos is transferred from development plates to pads of stratification medium. Plates are sealed with parafilm and placed in the dark at 2-6° C. for four weeks. After stratification, the mature somatic embryos are removed from plates and may be inserted into manufactured seed for subsequent germination and seedling establishment, or may be directly germinated.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method of multiplying pine or fir embryogenic tissue, the method comprising continuously culturing pine or fir embryogenic tissue in a liquid multiplication medium in a culture vessel for a time period of at least two weeks to six months, wherein continuous culture is effected by periodically supplementing the liquid multiplication medium in the culture vessel with successive additions of an additional volume of liquid multiplication medium, wherein the additional volumes of liquid multiplication medium periodically added to the culture vessel cumulatively increase the total volume of liquid multiplication medium in the culture vessel.

2. The method of claim 1, wherein the embryogenic tissue consists essentially of embryonal suspensor masses.

3. The method of claim 1, wherein the embryogenic tissue is Loblolly Pine embryogenic tissue.

4. The method of claim 1, wherein the embryogenic tissue is Douglas Fir embryogenic tissue.

5. The method of claim 1, wherein the additional volume of liquid multiplication medium is added once per week to the cultured embryogenic tissue in the culture vessel.

6. The method of claim 5, wherein the additional volume of liquid multiplication medium is added once per week to the cultured embryogenic tissue in the culture vessel for a time period of from two weeks to ten weeks.

7. The method of claim 1, wherein the ratio of the volume of pine embryogenic tissue in the culture vessel to the volume of additional liquid multiplication medium is from about 1:2 to about 1:5.

8. The method of claim 1, wherein the ratio of the volume of pine embryogenic tissue in the culture vessel to the volume of additional liquid multiplication medium is from about 1:4 to about 1:5.

9. The method of claim 1, wherein the ratio of the volume of Douglas fir embryogenic tissue in the culture vessel to the volume of additional liquid multiplication medium is 1:9.

* * * * *